United States Patent
Ivanova et al.

(10) Patent No.: US 10,792,244 B2
(45) Date of Patent: Oct. 6, 2020

(54) PARENTERAL SUSTAINED-RELEASE DELIVERY OF CARVEDILOL DISPERSE SYSTEMS

(71) Applicant: ASCENDIA PHARMACEUTICALS, LLC, North Brunswick, NJ (US)

(72) Inventors: Vera Ivanova, Cockkeysville, MD (US); Kaoru Maeda, South Plainfield, NJ (US); Wan Wang, New Brunswick, NJ (US); Dongwei Guo, Highland Park, NJ (US); Jingjun Huang, Monmouth Junction, NJ (US)

(73) Assignee: ASCENDIA PHARMACEUTICALS, LLC., North Brunswick, NJ (US)

( * ) Notice: Subject to any disclaimer, the term of this patent is extended or adjusted under 35 U.S.C. 154(b) by 0 days.

(21) Appl. No.: 16/429,693

(22) Filed: Jun. 3, 2019

(65) Prior Publication Data

US 2020/0000706 A1    Jan. 2, 2020

Related U.S. Application Data

(63) Continuation of application No. 15/621,844, filed on Jun. 13, 2017, now abandoned.

(60) Provisional application No. 62/349,390, filed on Jun. 13, 2016.

(51) Int. Cl.
| | |
|---|---|
| *A61K 9/00* | (2006.01) |
| *A61K 9/51* | (2006.01) |
| *A61K 9/50* | (2006.01) |
| *A61K 31/404* | (2006.01) |
| *A61K 9/127* | (2006.01) |
| *A61K 9/20* | (2006.01) |

(52) U.S. Cl.
CPC .......... *A61K 9/0002* (2013.01); *A61K 9/0019* (2013.01); *A61K 9/1272* (2013.01); *A61K 9/2072* (2013.01); *A61K 9/5031* (2013.01); *A61K 9/5146* (2013.01); *A61K 9/5153* (2013.01); *A61K 31/404* (2013.01); *A61K 9/2013* (2013.01)

(58) Field of Classification Search
CPC ... A61K 9/00; A61K 9/50; A61K 9/51; A61K 31/404; A61K 9/127; A61K 9/20
See application file for complete search history.

(56) References Cited

U.S. PATENT DOCUMENTS

| | | |
|---|---|---|
| 5,576,016 A | 11/1996 | Amselem et al. |
| 5,744,158 A | 4/1998 | Mayer et al. |
| 6,284,763 B1 | 9/2001 | Adams et al. |
| 7,179,484 B2 | 2/2007 | Singh |
| 7,235,237 B2 | 6/2007 | Loscalzo et al. |
| 2003/0068365 A1 | 4/2003 | Suvanprakorn et al. |
| 2004/0224012 A1 | 11/2004 | Suvanprakorn et al. |
| 2005/0143378 A1 | 6/2005 | Yun et al. |
| 2006/0034847 A1 | 2/2006 | Yun et al. |
| 2006/0116721 A1 | 6/2006 | Yun et al. |
| 2009/0148498 A1 | 6/2009 | Libin et al. |
| 2011/0118189 A1 | 5/2011 | Farr et al. |
| 2013/0337051 A1 | 12/2013 | Gaillard et al. |

FOREIGN PATENT DOCUMENTS

| | | |
|---|---|---|
| WO | 1994026252 | 11/1994 |
| WO | 2003030818 A2 | 4/2003 |
| WO | 2005051322 A2 | 6/2005 |
| WO | 2014018932 A2 | 1/2014 |
| WO | 2017218576 A1 | 12/2017 |

OTHER PUBLICATIONS

Written Opinion, dated Aug. 4, 2017, for PCT Application No. PCT/US2017/037311, International Filing Date Jun. 13, 2017, consisting of 3 pages.
International Search Report, dated Sep. 21, 2017, for PCT Application No. PCT/US2017/037311, International Filing Date Jun. 13, 2017, consisting of 2 pages.
International Preliminary Report on Patentability, dated Dec. 18, 2018, for PCT Application No. PCT/US2017/037311, International Filing Date Jun. 13, 2017, consisting of 4 pages.

*Primary Examiner* — Shirley V Gembeh
(74) *Attorney, Agent, or Firm* — Gearhart Law LLC

(57) ABSTRACT

Carvedilol parenteral sustained release systems by IV infusion, injection, or subcutaneous routes are disclosed. Preparation of carvedilol disperse systems such as liposomes, biodegradable microparticles or nanoparticles, and polymeric microparticles or nanoparticles have been presented in the present invention. Compositions containing carvedilol encapsulated in liposomes showed higher bioavailability and lower clearance rate than that of the free solution after intravenous administration. In vitro release of those liposomes in buffer solutions shows drug extended release over 48 hours, and correspondingly the in vivo animal data shows that parenteral administration of carvedilol encapsulated in liposomal materials has sustained release PK profile.

10 Claims, 6 Drawing Sheets

Figure 4. Size distribution of four types of Carvedilol/PL(G)A nanoparticles
Carvedilol_Resomer R203H (2% PVA)
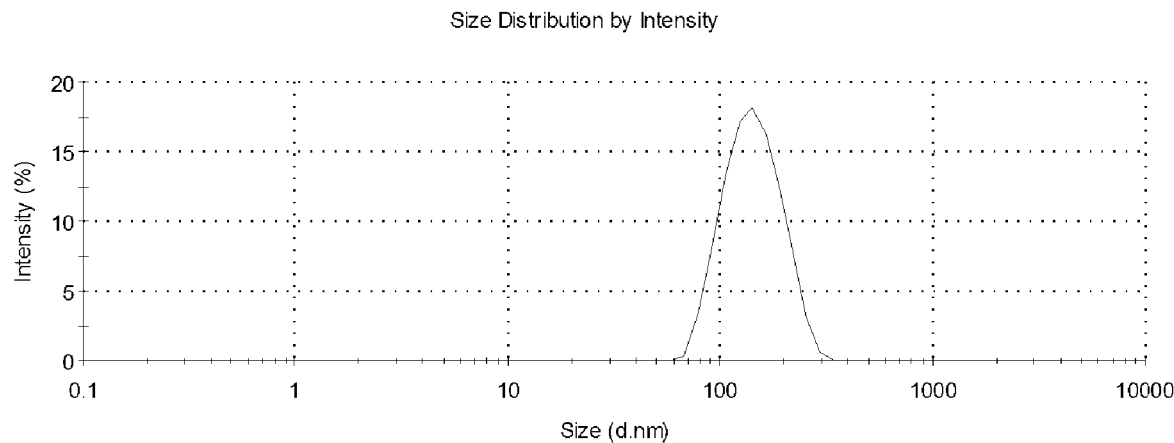
Carvedilol_Resomer RG502H (2% PVA)
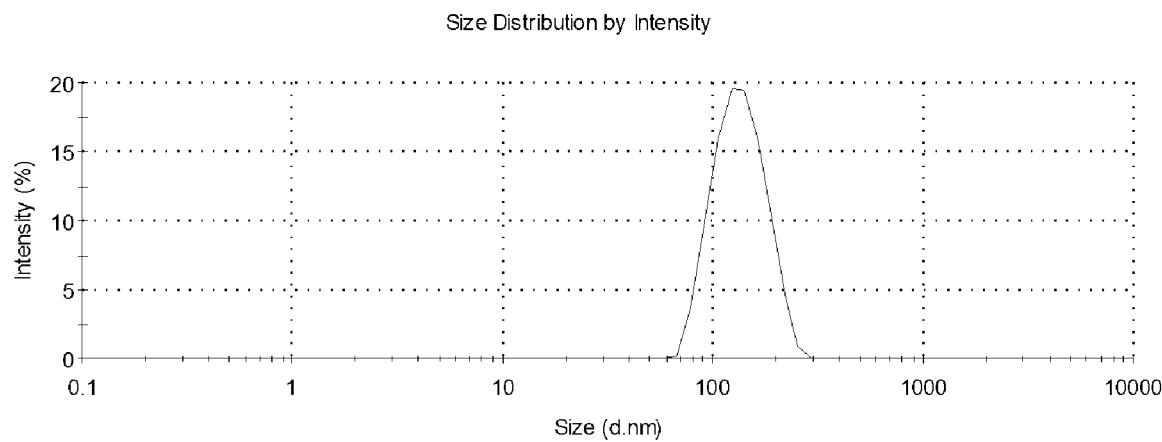
Carvedilol_Resomer Select 100DL mPEG 5000 (25% PEG) (2% PVA)
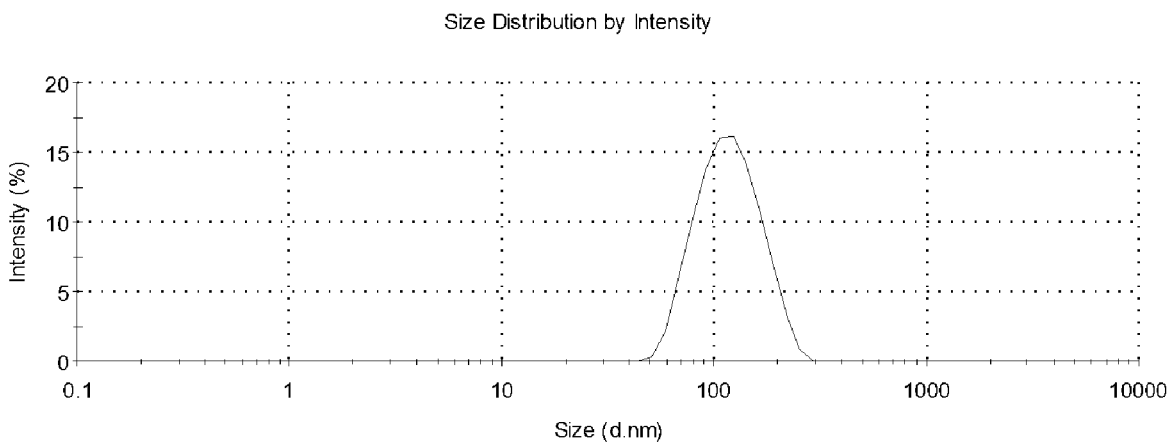

Carvedilol_Resomer R203H (1% PVA+10% PEG 4500)
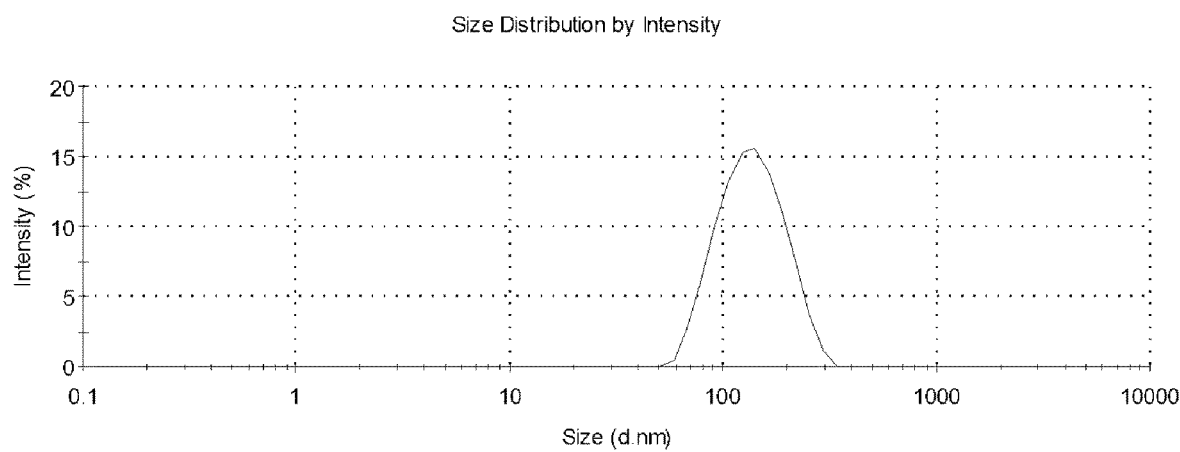
Figure 4 (continued). Size distribution of four types of Carvedilol/PL(G)A nanoparticles

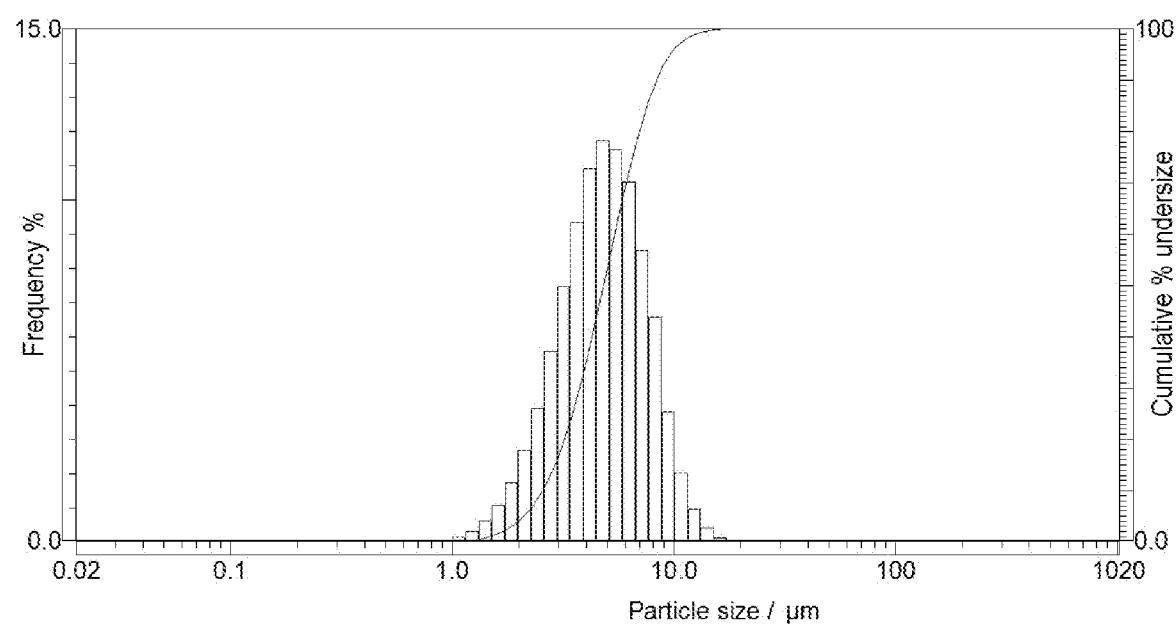
Figure 5. Microparticle size distribution

PARENTERAL SUSTAINED-RELEASE DELIVERY OF CARVEDILOL DISPERSE SYSTEMS

CLAIM OF PRIORITY

This patent application claims priority to U.S. application Ser. No. 15/621,844 filed on Jun. 13, 2017 which claims priority to U.S. provisional application Ser. No. 62/349,390 which was filed on Jun. 13, 2016 and the contents of both of which are herein incorporated by reference in its entirety.

FIELD OF THE EMBODIMENTS

The embodiments of the present invention relate to the use of carvedilol long-acting disperse systems for parenteral administration of carvedilol to efficiently manage patients with hypertension, heart failure, and left ventricular dysfunction.

BACKGROUND OF THE EMBODIMENTS

In a hypertensive emergency, patients experience elevated blood pressure that could lead to damage to the brain, kidney, or cardiovascular system. Damage to these target-organs often produce myocardial ischemia, hypertensive encephalopathy, cerebral edema, renal failure that can be fatal. First-line drugs that are typically used for IV infusion for rapid onset includes nitroprusside, fenoldopam, nicardipine, labetalol. These drugs can produce fast onset of lowering blood pressure that could lead to hypotension in patients. Nitrates, such as nitroprusside, are rapidly broken down into nitric oxide and cyanide that can produce cyanide toxicity in some patients.

Carvedilol is a non-selective β and α adrenergic receptor blocker with two active enantiomers that are responsible for the non-selectivity. Primary mechanism of action is inhibiting β-blocker receptors on myocytes slowing down the contractility of the heart thus lowering heart rate. Another mechanism of action is through blocking α-receptors that cause vasodilation. Currently, carvedilol is available only in immediate release oral tablets twice daily and oral controlled release once daily capsules. There is no parenteral dosage form of carvedilol available in market. Oral administration of carvedilol could potentially present a challenge for patients under acute care conditions, because oral dosage forms normally have a delay in drug onset due to the absorption process in GI tract, and carvedilol by oral administration has extensive first-pass metabolism that results in an oral bioavailability of only 25%-35%; Besides, side effects associated with carvedilol from oral dosage forms are frequently reported in patients taking those medicines. Therefore, a parenteral formulation of carvedilol with a rapid onset and yet a sustained release characteristics In-Vivo is desirable for management of inpatients with acute cardiovascular events.

Patent application US2002/0169199A1 disclosed a ready to use carvedilol injectable solution, however a higher rate of incident is expected due to a higher $C_{max}$ resulted from the IV injection of the solution form and organic solvent used to solubilize carvedilol.

U.S. Pat. No. 8,367,112 B2 disclosed carvedilol nanoparticles (with diameter less than 2000 nm), which is stabilized by a surface stabilizer absorbed to the surface of the carvedilol particles for improvement of dissolution rate and bioavailability. However, its application in sustained release by parenteral route was not disclosed.

SUMMARY OF THE EMBODIMENTS

The embodiments of the present invention are directed at formulating parenteral drug delivery systems of carvedilol, including but not limited to liposome, biodegradable micro/nanoparticles, micelles, and polymeric micro/nanoparticles, etc., having extended in vitro or in vivo carvedilol release and longer in vivo residence time than the free-carvedilol solution.

In one of the embodiments of the present invention, there is provided a parenteral drug delivery composition for sustained release, comprising a non-selective β-adrenergic receptor blocker, an α-adrenergic receptor blocker, or an α-β adrenergic receptor blocker, wherein the adrenergic receptor blocker is encapsulated inside microparticles or nanoparticles.

In one aspect of the embodiment, the non-selective β-, α-, or α-β adrenergic receptor blocker of the composition provided is carvedilol or its metabolites.

In another aspect of the embodiment, the composition provided is a liposome formulation.

In yet another aspect of the embodiment, the microparticles or nanoparticles of the composition provided are biodegradable.

In still another aspect of the embodiment, the microparticles or nanoparticles of the composition provided are polymeric.

In another embodiment of the present invention, there is provided a composition, wherein (i) the liposome formulation contains 0.001 to 10% percent (m/m) carvedilol or a pharmacologically acceptable salt thereof, (ii) the liposome formulation is in a size range of 0.02 microns to 0.9 microns in diameter, and (iii) the liposome formulation provides a longer residence time of the carvedilol in vivo, as compared to a free-carvedilol solution administered parenterally.

In one aspect of the embodiment, the liposome formulation of the composition provided before dosing includes between about 0.01 to 90 mole percent phospholipid(s), 0.01 to 70 mole percent cholesterol, and between about 0.01 to 90 mole percent of a negatively charged phospholipid.

The composition of claim 5, wherein a Z-average of a liposome mean diameter is less than 500 nm, preferably less than 300 nm, more preferably less than 200 nm, or even more preferably less than 100 nm.

In another aspect of the embodiment, the liposome of the composition provided exhibits an in vitro release of 80% of total drug for a minimum of 2 hours, preferably an in vitro release of 80% of total drug for a minimum of 6 hours.

In yet another embodiment of the present invention, there is provided a composition, wherein (i) the biodegradable formulation contains 0.001 to 30.0 percent (m/m) of carvedilol or a pharmacologically acceptable salt thereof, (ii) the microparticles or nanoparticles are in the size range of 0.02 to 20 microns in diameter, and (iii) the biodegradable formulation provides a longer residence time of the carvedilol in vivo, as compared to a free-carvedilol solution administered parenterally.

In one aspect of the embodiment, the biodegradable formulation of the composition provided includes about 0.001% to 30% m/m of carvedilol or a pharmacologically acceptable salt thereof, and the drug loading in the microparticles or nanoparticles is in the range of 0.1% to 90%, preferably 1% to 50%, and more preferably 10% to 30% (m/m).

In another aspect of the embodiment, a Z-average of a mean diameter of the microparticles or nanoparticles of the composition provided is less than 20 micron, preferably less than 1000 nm, more preferably less than 500 nm, still more preferably less than 300 nm, even more preferably less than 200 nm, or much more preferably less than 100 nm.

In yet another aspect of the embodiment, the microparticles or nanoparticles of the composition provided exhibits an in vitro release of 80% of total drug for a minimum of 2 hours, preferably an in vitro release of 80% of total drug for a minimum of 6 hours.

In yet another embodiment of the present invention, there is provided a composition, wherein (i) the polymeric microparticles or nanoparticles suspension contains 0.001% to 50% (m/m) carvedilol or a pharmacologically acceptable salt thereof, (ii) the polymeric microparticles or nanoparticles are in a size range of 0.02 microns to 50 microns in diameter, and (iii) the polymeric microparticles or nanoparticles provide a longer residence time of the carvedilol in vivo as compared to a free-carvedilol solution administered parenterally.

In one aspect of the embodiment, the microparticles or nanoparticles of the composition provided contain 0.001 to 50% m/m of carvedilol, and a weight ratio of carvedilol to the polymer(s) is 1:1 to 1:100, preferably 1:20 to 1:1000, and more preferably 1:10 to 1:100.

In another aspect of the embodiment, a Z-average of a mean diameter of the microparticles or nanoparticles of the composition provided is less than 50 micron, preferably less than 10 micron, more preferably less than 1 micron, still more preferably less than 500 nm, even more preferably less than 300 nm, much more preferably less than 200 nm, or even much more preferably less than 100 nm.

In still another embodiment of the present invention, there is provided a pharmaceutical composition for use in a parenteral drug delivery system for sustained release of carvedilol, wherein the composition being administered is for treating mild to severe congestive heart failure (CHF), left ventricular dysfunction (LVD) following heart attack in human or animals who are otherwise stable, and for treating high blood pressure for human or animals under emergence and intense care or who cannot swallow an oral dosage form.

It is one of the objects for the present invention to provide a composition containing carvedilol (or a pharmacologically acceptable analog, derivative, or salt thereof) encapsulated in liposomes by using passive loading and active loading methods. As revealed by the results disclosed in the present application that carvedilol can efficiently be encapsulated into those parenteral delivery systems. The animal study showed that those formulations have efficient drug loading and sustained drug release for injectable delivery system when compared to free-carvedilol form given by intravenous administration.

BRIEF DESCRIPTION OF THE DRAWINGS

FIG. 4. Particle size distribution of plga nanoparticles of different types of polymer.

FIG. 5. Microparticle size distribution of polymeric microparticles of Example 14.

DESCRIPTION OF THE PREFERRED EMBODIMENTS

Definition

Figure 1:
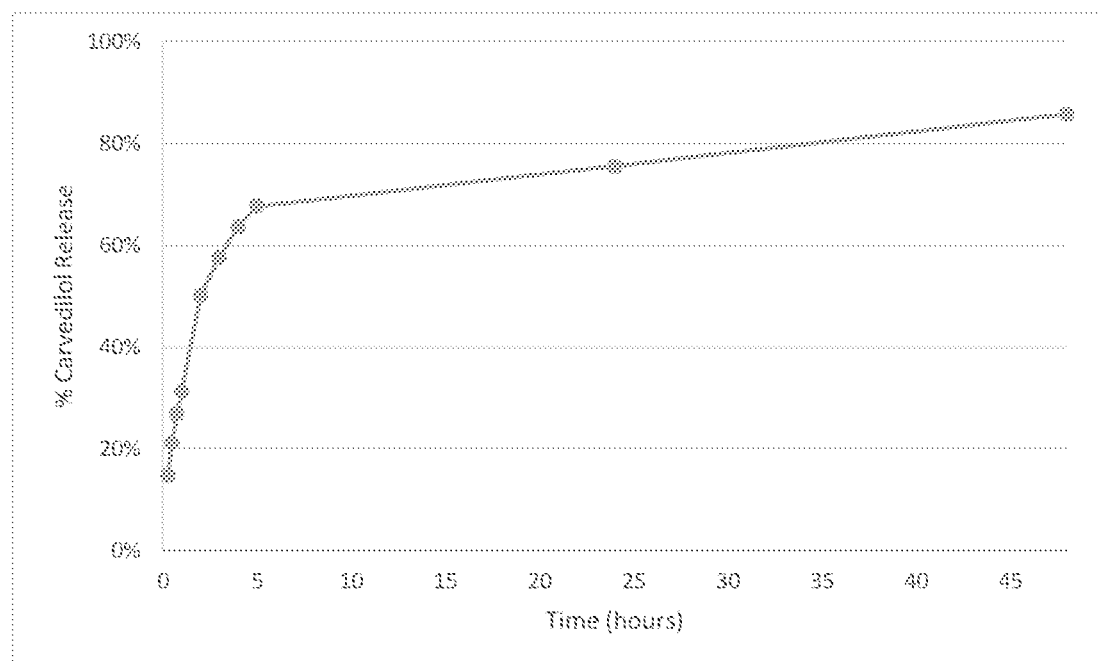
FIG. 1. In vitro dissolution profile of carvedilol liposome formulation prepared by active loading method.

Microparticles are a microscopic particle, which has a size range of 1 micron and 1000 micron.

Nanoparticles are a nanoscale particle, which has a size range of <1 micron to 1 nanometer.

Liposome

A liposome is a spherical vesicle having at least one lipid bilayer, which fall in the category of microparticles or nanoparticles. Liposomes can be prepared by disrupting biological membranes (such as by sonication). Liposomes are most often composed of phospholipids, especially phosphatidylcholine, but may also include other lipids, such as egg phosphatidylethanolamine, so long as they are compatible with lipid bilayer structure. Lipid complexation with drug and other materials is also regarded as liposome in this invention. A liposome design may employ surface ligands for attaching to unhealthy tissue. The drug could be incorporated into the liposome in either hydrophilic or hydrophobic region or both. The major types of liposomes are the multilamellar vesicles (MLV, with several lamellar phase lipid bilayers), the small unilamellar liposome vesicles (SUV, with one lipid bilayer), the large unilamellar vesicles (LUV), and the cochleate vesicles. A less desirable form are multivesicular liposomes in which one vesicle contains one or more smaller vesicles.

Liposomes are colloidal nanocarriers that can be administered by IV and injections. Liposomes hold great promise in delivering safely therapeutic agents due to their advantageous properties of having excellent physical stability, controlled release, encapsulation of hydrophilic and hydrophobic drugs, large surface area, and site specific targeting. Liposomal formulation of doxorubicin already possesses higher safety to the cancer patients when compared to its alternative formulations.

Liposome Preparation

A. Non-Selective Adrenergic Receptor Blockers

Adrenergic receptor blockers can be divided into, at the least, β-adrenergic receptor blockers, α-adrenergic receptor blockers, or α-β adrenergic receptor blockers. Among them are β-adrenergic receptor blockers, which medications reduce the workload on a patient's heart and open the patient's blood vessels, causing the heart to beat slower and with less force. β-adrenergic receptor blockers include acebutolol (Sectral), atenolol (Tenormin) and others. Orally administered β-adrenergic receptor include: Acebutolol (Sectral), Atenolol (Tenormin), Bisoprolol (Zebeta), Metoprolol (Lopressor, Toprol-XL), Nadolol (Corgard), Nebivolol (Bystolic), Propranolol (Inderal LA, InnoPran XL).

α-adrenergic receptor blockers are medications that reduce nerve impulses to blood vessels, reducing the effects of natural chemicals that narrow blood vessels. α-adrenergic receptor blockers include doxazosin (Cardura), prazosin (Minipress) and others.

α-β adrenergic receptor blockers are medications that, in addition to reducing nerve impulses to blood vessels, slow the heartbeat to reduce the amount of blood that must be pumped through the vessels. α-β adrenergic receptor blockers include carvedilol (Coreg) and labetalol (Trandate).

Carvedilol

The drug, carvedilol (±)-[3-(9H-carbazol-4-yloxy)-2-hydroxypropyl][2-(2-ethoxyphenoxy)ethyl] amine, used in preparing one of the compositions of the present invention is a non-selective β- and α-adrenergic receptor blocker with two active enantiomers with a $pK_a$ of 7.8. Carvedilol has poor aqueous solubility and undergoes significant first-pass metabolism. Alternative route of administration has been the main driving force for developing drug delivery system for optimal therapeutic effect.

Carvedilol has three active metabolites. Compared with Carvedilol, these metabolites exhibit only one-tenth of the vasodilating effect of the parent compound. However, the 4'hydroxyphenyl metabolite is about 13-fold more potent in ß-blockade than the parent compound. The metabolite desmethylcarvedilol is approximately 2.5 times more potent than Carvedilol as a β-adrenoceptor antagonist, 4-hydroxyphenyl-carvedilol is approximately 13 times more potent, and 5-hydroxyphenyl-carvedilol is approximately one-half as potent as carvedilol itself Hoffman (2001), Tenero et al (2000).

Liposomes are colloidal nanocarriers that can be administered by IV and injections. Liposomes hold great promise in delivering therapeutic agents safely due to their advantageous properties of having excellent physical stability, controlled release, encapsulation of hydrophilic and hydrophobic drugs, large surface area, and site specific targeting. Liposomal formulation of doxorubicin already possesses higher safety to the cancer patients when compared to its alternative formulations. Carvedilol is a mildly basic hydrophobic drug, hence making it difficult to deliver parenterally. This calls for an optimal formulated drug delivery system. Liposomes can be readily used in injectable dosage forms due to their nano-size. In addition, liposomes can have sustained release of the drug. They are made of biodegradable phospholipids that are physiologically well tolerated.

The carvedilol ratio (g/g) to the liposomal materials can range from 9.9:0.1 to 0.01:10, preferably from 1:1 to 0.1:10, more preferably from 1:2 to 0.1:10, still more preferably from 01:3 to 0.1:10, and even more preferably from 1:4 to 0.1:10.

B. Lipid Components

The liposomes are prepared from standard vesicle-forming lipids, which generally include neutral and negative phospholipids, such as phosphatidylcholine (PC) and phosphatidylglycerol (PG), respectively and sterols such as cholesterol. The selection of lipids is guided by considerations of (a) drug-release rate in vitro and in vivo, (b) drug encapsulation efficiency, and (c) liposome toxicity. From studies below, it will be seen neutral and negative phospholipids in combination or without sterol, such as cholesterol, were explored to determine their influence on these four main factors. With the addition of negatively charged phospholipids, the in vivo carvedilol release from liposomes was higher than liposomes with only neutral phospholipids. From in vitro release, it could be seen the carvedilol release from liposomes were slower when liposomes contained only phospholipids and no cholesterol.

The range of mole percent of phospholipids could be from 0.01% to 100%, preferably from 10 to 90%, more preferably from 20 to 80%, still more preferably from 30 to 70%, and even more preferably from 40 to 60%. The mole percentage of cholesterol could range from 00.0% to 100%, preferably from 10 to 90%, more preferably from 20 to 80%, still preferably from 30 to 70%, and even more preferably from 40 to 60%. Drug entrapment efficiency and drug retention were good when liposomes contain from 50 to 55 mole percent phospholipids, either neutral and/or negative phospholipids, and from 40 to 45 mole percent cholesterol. With these lipids components, no in vivo toxicity was observed.

C. Liposome Preparation

In one embodiment, carvedilol and vesicle-forming lipids were dissolved in an organic solvent, ethanol, which was injected into an aqueous medium. The multilamellar vesicles were processed to form unilamellar vesicles of about 0.2 microns. The produced vesicles contained carvedilol concentration ranging from 0.01 to 10 mg/mL, and preferably from about 0.1 to 1 mg/mL. The aqueous media used in reconstituting the dried lipid or lipid/carvedilol are physiologically compatible saline or buffer solutions.

In one embodiment, a thin-film hydration method, an active loading method and a passive loading method were used to prepare liposomes presented herein. In one method, vesicle-forming lipids with or without carvedilol are dissolved in organic solvent and dried to create a thin film. The film is then reconstituted in aqueous media to form liposomes. In one embodiment, the vesicle-forming lipids are dissolved in an organic solvent and then the solvent is removed to create a lipid film. The film is reconstituted in aqueous media to form multilamellar vesicles which are then processed by either extrusion or by high pressure homogenization. The unilamellar vesicles are then loaded with carvedilol. This produces vesicles having a carvedilol concentration of about 0.01 to 10 mg/mL, preferably from 0.1 to 1 mg/mL, and most preferably about 0.3 to 0.5 mg/mL D. Liposome Sizing The liposome suspension may be sized to achieve a selective size distribution of vesicles in a size range less than about 1 micron and preferably between about 0.02 to 0.6 microns, and most preferably between 0.05 to 0.2 microns. The sizing is done to extrude larger liposomes and to produce a defined size range. There are numbers of methods available to reduce sizes and size heterogeneity of liposomes. By using mini-extruder as shown in Examples 1 and 2, the resulting unilamellar vesicles are less than 0.1 microns in size. Extrusion process of liposomes through a small-pore polycarbonate membranes can achieve a liposome size range of about 0.1 to 1 microns. There are numbers of small-pore sizes available for the polycarbonate membranes that can be used for sizing the vesicles. Homogenization, sonication, or microfluidization are other methods of sizing multilamellar vesicles into small unilamellar vesicles. In one embodiment, the multilamellar vesicles are circulated through a standard emulsion homogenizer multiple cycles until selected liposome sizes, typically ranging from 0.1 and 0.5 microns are observed.

E. Free Drug Removal

Free drug, the drug present in the total aqueous phase of the suspension can be removed to increase the ratio of liposome-encapsulated to free drug. Under the preparation conditions described in Example 2, for example, after removal of the free carvedilol by dialysis in saline, the liposomes incorporated between about 85% to 86% of the carvedilol in the total suspension.

Biodegradable Micro/Nanoparticles

Biodegradable micro/nanoparticles are micron to nano-sized particles comprised of drug and biodegradable polymer(s), wherein the drug is dispersed in the matrix of bio-degradable polymer(s). The Z-average mean diameter of the particles of this invention range from 100 micron to below 100 nm, preferably from 50 micron to 10 micron, more preferably from 10 to 2 micron, still more preferably from 2 micron to 500 nm, even preferably from 500 to 100 nm, and most preferably below 100 nm. Biodegradable polymers are a specific type of polymer that breaks down after its intended purpose to result in natural byproducts such as gases ($CO_2$, $N_2$), water, biomass, and inorganic salts inside of human body. The molecular weight can range from 500 to >100,000 Dalton. These polymers are found both naturally and synthetically made, and largely consist of ester, amide, and ether functional groups. Their properties and breakdown mechanism are determined by their exact structure. These polymers are often synthesized by condensation reactions, ring opening polymerization, and metal catalysts.

Biodegradable polymer including but is not limited to the following: Agro-polymers including polysaccharides, like starches found in potatoes or wood, and proteins, such as animal based whey or plant derived gluten. Polysaccharides consisting of glycosidic bonds, which take a hemiacetal of a saccharide and binds it to an alcohol via loss of water. Proteins are made from amino acids, which contain various functional groups. These amino acids come together again through condensation reactions to form peptide bonds, which consist of amide functional groups. Examples of biopolyesters includes polyhydroxybutyrate and polylactic acid. While polyesters dominate both the research and industrial focus on synthetic biodegradable polymers, other classes of polymers are also of interest. Polyanhydrides are an active area of research in drug delivery because they only degrade from the surface and so are able to release the drug they carry at a constant rate. Polyanhydrides can be made via a variety of methods also used in the synthesis of other polymers, including condensation, dehydrochlorination, dehydrative coupling, and ROP. Polyurethanes and poly (ester amide)s are used in biomaterials. Polyurethanes were initially used for their biocompatibility, durability, resilience, but are more recently being investigated for their biodegradability. Polyurethanes are typically synthesized using a diisocyanate, a diol, and a polymer chain extender.

The preferred biodegradable polymers are polyester polymers, particularly the Poly (lactic-co-glycolic acid) (PLGA) and poly lactic acid (PLA) and their derivatives. Poly (lactic-co-glycolic acid) (PLGA) is a member of the aliphatic polyester family of biodegradable biocompatible polymers. PLGA is a copolymer of poly lactic acid (PLA) and poly glycolic acid (PGA). Poly lactic acid contains an asymmetric α-carbon which is typically described as the D or L form. PLGA is generally an acronym for poly D,L-lactic-co-glycolic acid where D- and L-lactic acid forms are in equal ratio. PLGA undergoes hydrolysis in the body to produce the original monomers, lactic acid and glycolic acid (see structure below). These two monomers are by-products of various metabolic pathways in the body under normal physiological conditions.

PLGA has been a popular choice for drug delivery applications ever since its approval from FDA for use in humans. In particular, PLGA has been extensively studied for the development of devices for controlled delivery of small molecule drugs, proteins and other macromolecules in commercial use and in research. Additionally, it is possible to modify the physical properties of the polymer-drug matrix by controlling the relevant parameters such as polymer molecular weight, ratio of lactide to glycolide, surfactant, surface property and drug concentration to achieve desired drug release profile. Moreover, to further enhance the circulation time of PLGA encapsulated drugs and improve its bioavailability, various types of block copolymers of PL(G)A with poly ethylene glycol (PEG) have been developed. In diblock (PLGA-PEG) types, PEG chains orient themselves towards the external aqueous phase, thus surrounding the encapsulated species. This PEG corona acts as a barrier and reduces the interactions with foreign molecules by steric and hydrated repulsion, giving enhanced shelf stability.

Hydrophobic and hydrophilic drugs can be encapsulated in PLGA particles via emulsification-diffusion, solvent emulsion-evaporation, interfacial deposition and nanoprecipitation method. Specifically, oil-water (single) emulsion method is very popular to encapsulate hydrophobic compounds. Briefly, the drug is dissolved with polymer in an organic phase that is then emulsified with the aqueous phase mixed with surfactant to stabilize the system. Various emulsifiers have been tested such as Poly (vinyl alcohol), poloxamer, Vitamin-E TPGS, etc. High intensity sonication bursts facilitate the formation of small polymer-drug droplets. The resulting emulsion is then added into a larger aqueous phase and stirred for several hours, which allows the solvent to evaporate. The dried nanoparticles are then washed and collected via centrifugation. PLGA degrades slowly via hydrolysis in aqueous environments to modulate controlled release of encapsulated agents.

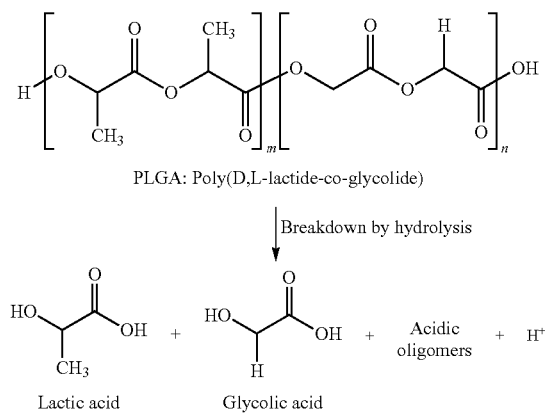

Chemical structure of PLGA and its hydrolysis products

Polymeric Micro/Nanoparticles

Polymeric micro/nanoparticles refer to micron to nano sized drug particles coated with layer(s) of polymer(s) and/or other materials. A polymer is a large molecule, or macromolecule, composed of many repeated subunits. The molecular weight can range from 500 to >100,000 Daltons. A biodegradable polymer defined in the biodegradable micro/nanoparticles section is preferred for use in this invention. The Z-average mean diameter of the polymeric particles of this invention range from 100 micron to below 100 nm, preferably from 50 micron to 10 micron, more preferably from 10 micron to 2 micron, still more preferably from 2 micron to 500 nm, even more preferably from 500 nm to 100 nm, and most preferably below 100 nm. Biodegradable polymeric nanoparticles where the drug is coated by polymeric materials are deemed to be very efficient drug delivery systems. It should be highlighted that the liberation of the polymer encapsulated drug can be carefully controlled by total surface area or the particle size, or the coating materials; and the drug concentration in the target site is maintained within the therapeutic window. Biodegradable polymers are considered as ideal biomaterials for the development of controlled- and sustained-release drug delivery systems as well as therapeutic devices. The present invention relates to injectable polymeric compositions, which can be used to improve the formulation injectability and stability. The remarkable feature of the present nano-formulation is aiming at enhanced treatment efficacy and sustained drug release. A further feature of the invention is reduced toxicity and improved patient compliance. Compared with commercially available carvedilol in twice daily immediate release tablets and once daily controlled release capsules, nano/microparticle-formulations by parenteral routes, such as SC, IM, IV or bolus injection, could potentially convert the oral route to the parenteral route with once-a-day dosing, once-a-week, once a month or once 2-6 months dosing by using sustained release dosage form, which shows promise to enhance patient compliance, and to decrease the side effects and toxicity.

The drug concentration in the polymeric micro/nanoparticle formulation ranges from 0.01 to 500 mg/ml, preferably from 0.1 to 300 mg/mL, more preferably from 1 to 100 mg/ml, and most preferably from 1 to 50 mg/ml.

The following non-limiting examples are provided to further illustrate the present invention.

Example 1 (Liposome-Passive Loading)

Materials

Carvedilol was obtained from Kinfon Pharma (Shanghai, China), egg PC (L-α-phosphatidylcholine) was obtained from Lipoid (Newark, N.J.), cholesterol was obtained from Avanti Lipids (Birmingham, Ala.), DMPC (1,2-dimyristoyl-sn-glycero-3-phosphocholine), DMPG (1,2-dimyristoyl-sn-glycero-3-phospho-(1'-rac-glycerol) and DSPE (1,2-distearoyl-sn-glycero-3-phosphoethanolamine-N-[amino(polyethylene glycol)-2000] (ammonium salt) were obtained from NOF America (White Plains, N.Y.). It should be noted that phospholipids were used in these experiments as they are readily available. Other chemicals which can result in similar compositions can also be used. The primary particle size of liposomal carvedilol was about 100 nm, for the parenteral administration.

Preparation Procedure

Liposomal carvedilol was synthesized by initially dissolving carvedilol in methanol and then dissolving lipids and drug in chloroform. Phospholipids DMPC, DMPG, DSPE were used in molar ration of (85:10:5). Briefly, lipids with or without drug were dissolved in 4 ml of chloroform. After which solvent evaporation was performed under stream of nitrogen gas at room temperature in round bottom test tube for 20 minutes. Subsequently, thin film was created at the bottom of the round bottom test tube which was stored in the vacuum desiccator for complete solvent evaporation overnight. Then each thin film formulation with and without carvedilol was resuspended in PBS at pH 7.4 and 37° C. It was vortexed for 5 minutes and rehydrated at 37° C. for 30 minutes. Liposomes that were produced up to this stage are large unilamellar vesicles (LUVs) and multilamellar vesicles (MLVs). Subsequently, the large liposomal carvedilol and empty liposomes were extruded gradually through 200 nm and 100 nm polycarbonate membranes using EmulsiFlex-C5 high pressure homogenizer Avestin, Inc. (Ottawa, ON, Canada). Finally, liposomal carvedilol was passed through 0.22 μm syringe filter for sterility.

Example 2 (Liposome-Passive Loading)

In another lipid formulation, lipids were dissolved in 10% ethanol of the formulation. Lipids molar concentration was 50:45:5 for DMPC:Cholesterol:DSPE (F1) and 55:45 for EPC:Cholesterol (F2). Briefly the lipid ethanol solution was heated to 60° C. Then the ethanol solution was injected into saline (0.9% NaCl) aqueous media. Further, these liposomal formulations were subjected to high shear by using a high pressure homogenizer at 12,000 PSI through 10 cycles. The liposome formulations were filtered through 0.22 μm PTFE filters for sterilization. In the passive loading technique liposomes have to be separated further from non-encapsulated carvedilol. Liposome formulation was dialyzed in 0.9% saline. Liposome formulations formed prior to process show large size around 1 μm, however size is reduced after extrusion with preselected membranes. Liposomes 1 showed the same size and narrow polydispersity index indicating homogeneous dispersion of liposomal carvedilol with two different formulations of phospholipids (Table 1). Final average liposomal carvedilol size is observed around 75-150 nm range.

Drug loading (DL) capacity and encapsulation efficiency (EE) were determined by separating liposomes from aqueous phase containing non-associated carvedilol using Amicon® Ultra 50K membrane. The amount of free carvedilol in the supernatant was assayed. The drug load/assay were analyzed by reversed phase high performance liquid chromatography (RP-HPLC) and detected by ultra-violet (UV) absorbance. Carvedilol encapsulation efficiency was calculated as follows:

$$EE\% = \left(\frac{Wloaded}{Wtotal}\right) \times 100\%$$

TABLE 1

| Formulation | Particle size (nm) | PDI | DL (mg/ml) | EE % |
|---|---|---|---|---|
| F1 | 177.1 | 0.193 | 0.407 | 88.2 |
| F2 | 143 | 0.117 | 0.874 | 83.4 |

Both formulations had entrapment efficiency of about 80-90% and drug loading obtained was 0.4-0.8 mg/ml.

The liposomes described herein can also include or be prepared by other lipids from its family. Therefore, naturally occurring and semisynthetic phospholipids of fatty acid di-esters, phosphatidylcholine, phosphatidylglycerol, phosphatidic acid, phosphatidylethanolamine, phosphatidylserine, and sphingomyeline can be used. Examples of similar lipids that are preferred to be used are dimyristoyl-phosphatidylcholine (DMPC), dipalmitoyl-phosphatidylcholine (DPPC), distearoyl-phosphatidylcholine (DSPC), 1-palmitoyl-2-myristoyl-phosphatidylcholine (MPPC), diarachidoylphosphatidylglycerol (DAPG) and its alkali metal salts, dimyristoylphosphatidylglycerol (DMPG) and its alkali metal salts, dipalmitoylphosphatidylglycerol (DPPG) and its alkali metal salts, distrearoylphosphatidylglycerol (DSPG), dipalmitoylphosphatidic acid (DPPA), dipalmitoylphosphatidylethanolamine (DPPE), distearoylphosphatidylethanolamine (DSPE). It also includes modified phospholipids whereas hydrophilic head group is attached to another hydrophilic group, polyethylene glycol (PEG), such as in DSPE-PEG where ethanolamine head group is attached to various length of PEG moiety of molecular weight between 300 and 5000 Daltons.

Example 3 (Liposome-Active Loading)

Another method used for loading carvedilol inside was by creating pH gradient across liposome bilayer. First, lipids were solubilized in chloroform solvent which was evaporated. Thin film was rehydrated in 120 mM ammonium sulfate buffer. Buffer is utilized to establish interior aqueous chemical conditions. Alternate heating and vortexing followed by extrusion using mini-extruder, produced unilamellar liposomal vesicles. Empty liposomes were allowed to dialyze in external buffer saline to create pH gradient. Carvedilol was solubilized in 0.1N NaOH and added to the external media followed by incubation for 1 hour at 60 C.

Example 4 (Free Drug Determination for Active Loading Liposome Formulation)

An ethanol solution of vesicle-forming lipids containing 75.0 mg of DMPC, 31.3 mg of cholesterol and 28.4 mg of DSPE was prepared at 60° C. water bath. The lipid solution was injected into pH 3.6 0.1M citrate buffer. The final volume of the lipid solution was 10 mL. The multilamellar vesicle (MLV) dispersion was processed 10 cycles using a high-pressure homogenizer at 12,000 PSI. Once the liposomes became unilamellar, the liposomes were dialyzed in 0.9% w/v saline solution for 1 hour at ambient condition at 100 RPM. For dialysis, Spectra/Por® 6 membrane with molecular weight cutoff of 15,000 was utilized. To the same saline solution, which was heated to 37° C., 10.3 mg of carvedilol was dissolved and the liposomes were dialyzed for another 1 hour in the carvedilol solution. Then the liposomes were dialyzed in fresh 0.9% w/v saline solution for 24 hours to remove any un-encapsulated free carvedilol. The carvedilol containing liposomes had the following characteristics:
  (a) Total carvedilol in the liposomes was 0.0054 mg/mL;
  (b) After removing the free carvedilol, total carvedilol was 0.053 mg/mL Example 5 (Liposome-Active Loading Method)

An ethanol solution of vesicle-forming lipids containing 85.5 mg of EPC, 35.4 mg of cholesterol was prepared at 60° C. water bath. The lipid solution was injected into pH 3.6 0.1M citrate buffer. The final volume of the lipid solution was 10 mL. The multilamellar vesicle (MLV) dispersion was processed 10 cycles using a high-pressure homogenizer at 10,000 PSI. Once the liposomes became unilamellar, the liposomes were dialyzed in 25 mM HEPES saline solution for 4 hour at ambient condition at 350 RPM. For dialysis, Spectra/Por® 6 membrane with molecular weight cutoff of 15,000 was utilized. To the same HEPES saline solution, 60.1 mg of carvedilol was dissolved and the liposomes were dialyzed in the carvedilol solution. Following dialysis, the liposome formulation was filtered through 0.22 μm PTFE filter. In vitro dissolution of the liposome formulation was conducted. 2 mL of the liposome suspension was placed in a Spectra/Por® 6 membrane with molecular weight cutoff of 15,000. The liposome containing membrane was placed in 200 mL of pH 6.5 0.05M sodium phosphate solution containing 0.05% w/v tween 80. The dissolution medium was kept at 37° C. under constant stirring of 100 RPM. Samples were withdrawn at 0.25, 0.5, 0.75, 1, 2, 3, 4, 5, 24 and 48 hours. Dissolution results are presented in FIG. 1. Liposomes exhibit carvedilol release over 48-hour period and reaches more than 80% carvedilol release at 48 hours. The carvedilol containing liposomes described had the following characteristics:
  (a) Total carvedilol in the liposomes was 0.48 mg/mL before filtration;
  (b) After filtration, total carvedilol was 0.47 mg/mL;
  (c) The size distribution of was between 0.05 and 0.3 microns.

Example 6 (Freeze Thaw for Formulation 1)

An ethanol solution of vesicle-forming lipids containing 75.4 mg DMPC, 31.4 mg cholesterol, 28.6 mg DSPE and 10.4 mg of carvedilol was prepared at 60° C. water bath. The lipid solution was injected into 0.9% w/v saline solution at room temperature. The final MLV contained carvedilol at 1 mg/mL in a total of 10 mL volume. The MLV dispersion was further processed 10 cycles using a high-pressure homogenizer at 12,000 PSI. The sized liposomes were sterilized by filtration through a 0.22 μm polytetrafluoroethylene (PTFE) filter. The sterilized liposomes were stored in glass vials at 4° C. and −20° C. The carvedilol containing liposomes had the following characteristics:
  (a) Total carvedilol in the liposomes was greater than 54% of the initial amount of drug;
  (b) The size distribution of was between 0.04 and 0.9 microns (determined by dynamic laser light scattering technique);
  (c) The total carvedilol in the thawed liposomes after 3 days of storage in −20° C. was greater than 56% of the initial amount of drug;
  (d) The thawed liposomes size distribution was between 0.09 and 0.5 microns.

Example 7 (Freeze Thaw for Formulation 2)

An ethanol solution of vesicle-forming lipids containing 86.6 mg EPC and 35.5 mg cholesterol and 10 mg of carvedilol was prepared at 60° C. water bath. The lipid solution was injected into 0.9% w/v aqueous saline solution at room temperature. The final multilamellar vesicle (MLV) contained carvedilol at 1 mg/mL in a total of 10 mL volume. The MLV dispersion was further processed 10 cycles using a high-pressure homogenizer at 12,000 PSI. The sized liposomes were sterilized by filtration through a 0.22 μm polytetrafluoroethylene (PTFE) filter. The sterilized liposomes were stored in glass vials at 4° C. and −20° C. The carvedilol containing liposomes had the following characteristics:
  (a) Total carvedilol in the liposomes was greater than 68% of the initial amount of drug;
  (b) The size distribution of was between 0.09 and 0.5 microns;
  (c) The total carvedilol in the thawed liposomes after 3 days of storage in −20° C. was greater than 68% of the initial amount of drug;
  (d) The thawed liposomes size distribution was between 0.08 and 0.6 microns.

Example 8 (PK Study Formulation 1)

An ethanol solution of vesicle-forming lipids containing 172.8 mg EPC and 71.7 mg cholesterol and 20.1 mg of carvedilol was prepared at 60° C. water bath. The lipid solution was injected into 0.9% w/v aqueous saline solution at room temperature. The final multilamellar vesicle (MLV) contained carvedilol at 1 mg/mL in a total of 20 mL volume. The MLV dispersion was further processed 10 cycles using a high-pressure homogenizer at 12,000 PSI. The sized liposomes were sterilized by filtration through a 0.22 µm polytetrafluoroethylene (PTFE) filter. The sterilized liposomes were stored in glass vials at 4° C. and −20° C. The carvedilol containing liposomes had the following characteristics:
  (a) Total carvedilol in the liposomes was greater than 52% of the initial amount of drug;
  (b) The size distribution of was between 0.06 and 0.5 microns;
  (c) The total carvedilol in the thawed liposomes after 1 day of storage in −20° C. was greater than 52% of the initial amount of drug;
  (d) The thawed liposomes size distribution was between 0.07 and 0.6 microns.

Example 9 (PK Formulation 2)

An ethanol solution of vesicle-forming lipids containing 225.7 mg DMPC, 91.9 mg cholesterol, 86.6 mg DSPE and 29.4 mg of carvedilol was prepared at 60° C. water bath. The lipid solution was injected into 0.9% w/v saline solution at room temperature. The final MLV contained carvedilol at 1 mg/mL in a total of 30 mL volume. The MLV dispersion was further processed 10 cycles using a high-pressure homogenizer at 12,000 PSI. The sized liposomes were sterilized by filtration through a 0.22 µm polytetrafluoroethylene (PTFE) filter. The sterilized liposomes were stored in glass vials at 4° C. and −20° C. The carvedilol containing liposomes had the following characteristics:
  (a) Total carvedilol in the liposomes was greater than 32% of the initial amount of drug;
  (b) The size distribution of was between 0.02 and 0.5 microns (determined by dynamic laser light scattering technique);
  (c) The total carvedilol in the thawed liposomes after 3 days of storage in −20° C. was greater than 30% of the initial amount of drug;
  (d) The thawed liposomes size distribution was between 0.07 and 0.4 microns Example 10 (In Vitro Dissolution of Examples 8&9)

Figure 2:
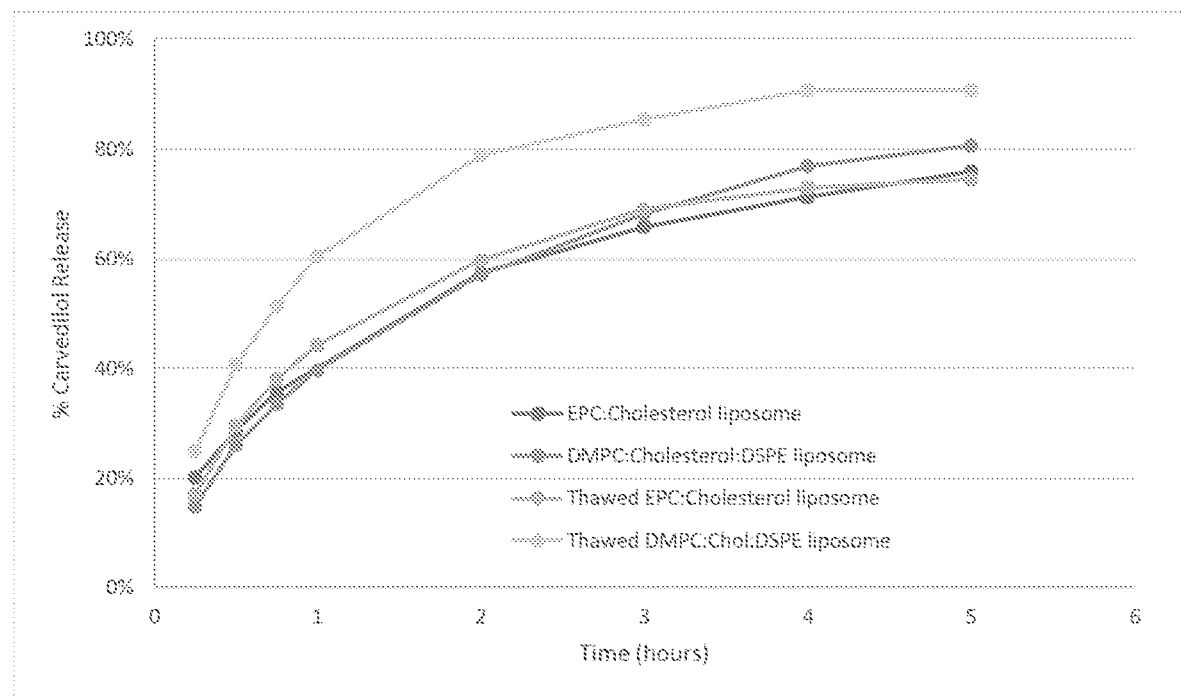
FIG. 2. In vitro dissolution profiles of carvedilol liposome formulations from Example 8 and 9, before and after freeze-thaw.

In vitro dissolution study was conducted using liposomes described in Examples 8 and 9. 1 mL of the liposome suspension was placed in a Spectra/Por® 6 membrane with molecular weight cutoff of 15,000. The liposome containing membrane was placed in 400 mL of pH 6.5 0.05M sodium phosphate solution containing 0.05% w/v tween 80. The dissolution medium was kept at 37° C. under constant stirring of 100 RPM. Samples were withdrawn at 15, 30, 45, 60, 120, 180, 240 and 300 minutes. Dissolution results are presented in FIG. 2. Except for a slight increased rate of carvedilol release observed in the thawed liposomes prepared in Example 8, the liposomes exhibit similar carvedilol release over 6-hour period.

Example 11 (PK Study)

Figure 3:
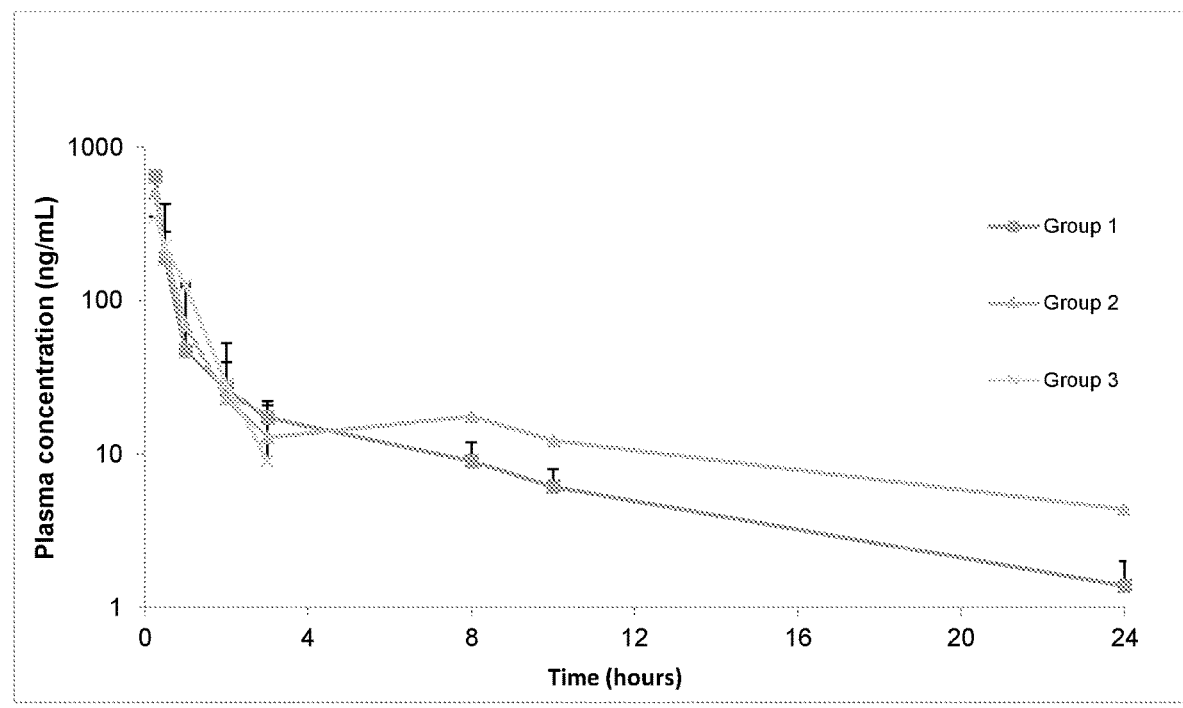
FIG. 3. Mean time-plasma concentration profiles of Carvedilol in rats following a single iv administration (semi-log scale).

Single Injection of Carvedilol Liposomes and Free-Carvedilol Solution
Carvedilol liposomes were prepared as in Examples 8 and 9, to final carvedilol concentrations of 0.52 and 0.32 mg/mL. Free carvedilol was prepared in 20% w/w aqueous PEG 400 solution to final concentration of 0.46 mg/ml. 15 cannulated and non-cannulated, 9 and 6 rats respectively, Sprague-Dawley® male rats were divided into 3 groups. Each group received 2.5 mg/kg body weight dose of either carvedilol liposomes or free-carvedilol. Group 1 received thawed liposomes described in Example 8, group 2 received thawed liposomes described in Example 9 and group 3 received free-carvedilol solution. Treatment was administered intravenously. During the experiment, rats were inspected twice daily for vitality and as needed after dosing and intermittently and vitals, including blood pressure, heart rate, and temperature, were recorded from the non-cannulated animals. Main vital signs were monitored prior to and at multiple time points after dose administration. Blood pressure and heart rate were measured using a non-invasive tail cuff system after a brief acclimation period. Blood samples (approximately 300-325 µL each) were collected from cannulated rats at each time point into tubes containing K2EDTA. Following centrifugation at 4° C., the plasma was collected and stored at −80° C. The blood sampling time points were as follows: prior to (PRE) and approximately 0.25, 0.5, 1, 2, 3, 8, 10 and 24 hours after dose administration. Samples were collected via Jugular Vein Cannulas. No adverse reaction was observed throughout the study as shown in Tables 3-5. As the mean-time plasma concentration profiles of carvedilol in rats are shown in FIG. 3, both carvedilol liposomes exhibited presence of carvedilol in plasma 24 hours after administration whereas the free-carvedilol solution showed carvedilol was cleared 3 hours after the dose was administered. As shown in Table 2, $C_{max}$, AUC and Half-life of carvedilol in liposomes were higher compared to those of the free-carvedilol in solution.

TABLE 2

| Treatment | Group | | Cmax (ng/mL) | Tmax (hr) | AUC(0-T) (ng/mL*h) | AUC(INF) (ng/mL*h) | T-HALF (hr) | CL (mL/min/kg) | Vss (L/kg) |
|---|---|---|---|---|---|---|---|---|---|
| Carvedilol (2.5 mg/kg) | Group 1 | Mean | 644 | 0.25 | 402 | 412 | 5.64 | 102.4 | 50.1 |
| | | SD | 237 | 0.00 | 61.7 | 58.5 | 0.24 | 14.6 | 9.1 |
| | Group 2 | Mean | 506 | 0.25 | 344 | 368 | 3.20 | 197.2 | 23.4 |
| | | SD | 394 | 0.00 | 274 | 301 | 4.53 | 174.1 | 18.6 |
| | Group 3 | Mean | 354 | 0.25 | 284 | 291 | 0.52 | 144.0 | 6.4 |
| | | SD | 51.3 | 0.00 | 23.0 | 29.8 | 0.11 | 14.2 | 0.7 |

TABLE 3

| | Systolic | Diastolic | MAP | HR (Beats/mm) | Temp (° F.) |
|---|---|---|---|---|---|
| Pre-Dose | 110 | 34 | 59 | 383 | 100 |
| 15 min | 97 | 37 | 57 | 371 | 99 |
| 30 min | 125 | 72 | 89 | 381 | 99 |
| 1 Hour | 120 | 69 | 86 | 391 | 99 |

TABLE 4

| | Systolic | Diastolic | MAP | HR (Beats/mm) | Temp (° F.) |
|---|---|---|---|---|---|
| Pre-Dose | 108 | 23 | 51 | 423 | 99 |
| 15 min | 98 | 42 | 61 | 365 | 99 |
| 30 min | 89 | 39 | 56 | 375 | 100 |
| 1 Hour | 104 | 47 | 86 | 391 | 100 |

TABLE 5

| | Systolic | Diastolic | MAP | HR (Beats/mm) | Temp (° F.) |
|---|---|---|---|---|---|
| Pre-Dose | 132 | 32 | 65 | 448 | 99 |
| 15 min | 125 | 48 | 73 | 354 | 98 |
| 30 min | 115 | 33 | 60 | 360 | 99 |
| 1 Hour | 126 | 40 | 69 | 363 | 99 |

9,000-10,000, 80% hydrolyzed), is chosen as water phase with surfactant. Other types of surfactants, such as poloxamer 188, poloxamer 407, Vitamin E-TPGS, didodecyldimethylammonium bromide (DMAB), sodium caprylate, Tween 20, Tween 80, PEG, etc. can also be used. As an example of surface modification, we also illustrate the addition of PEG into the water phase in a test tube. To make nanoparticle emulsion, the polymer/carvedilol solution is added dropwise into small amount of water phase (oil:water phase ratio is 1:7) while the water phase is on high vortex. After the entire polymer solution has been added, the formed emulsion is vortexed thoroughly for an additional 20 seconds. The mixture is immediately transferred to the ultrasonicator (Fisher Scientific Sonic Dismembrator Model 500). The emulsion is immersed in ice water and sonicated for 7 minutes (65% amplitude, 20 seconds on, 8 seconds off). Nanoparticle size is checked periodically using Malvern Nano-ZS zeta sizer. The emulsion is then poured into stirring bulk water phase (2% PVA) solution and stirred (600 rpm) at room temperature for at least 3 hours. For nanoparticle collection, dried nanoparticles are centrifuged in a fixed-angle rotor for 30 minutes at 14,000×g. The supernatant is discarded and nanoparticles are washed with ddH$_2$O. This process is repeated for three times. Then concentrated nanoparticle suspension is added into a Amicon® Ultra Centrifugal filter (50 kD cut-off) and centrifuged for 10 minutes at 14,000×g to remove free drug. The purified nanoparticles can be used freshly, stored at 4° C. for up to weeks or lyophilized after lyo- and cryo-protection with sucrose (10-30%). Drug loading is tested using HPLC.

PL(G)A/PL(G)A-PEG Type and formed nanoparticles

| | Polymer | | | | | | | Surfactant | | | Zeta |
|---|---|---|---|---|---|---|---|---|---|---|---|
| Polymer type | Description | M.W. | Viscosity | End Group | Tm | Tg | Half Life | Surfactant | Z. Average (d · nm) | PdI | potential (mV) |
| Resomer ®R 203 H | Poly(D,L-lactide) | 18,000-24,000 | 0.25-0.35 dL/g | acid terminated | | 48-52° C. | <6 mo | 2% PVA | 135.2 | 0.072 | −11.4 ± 0.6 |
| | | | | | | | | 1% PVA + 10% (w/w) PEG 4500 | 127.2 | 0.106 | −1.2 ± 0.1 |
| Resomer Select 100 DL mPEG 5000 (25% PEG) | Poly(D,L-lactide)-b-poly (ethylene glycol) methyl ether 5000 | 30,000 | 0.33-0.45 dL/g | | 48° C. | 9° C. | | 2% PVA | 110.3 | 0.090 | −4.1 ± 0.3 |
| Resomer ®RG 502H | lactide:glycolide 50:50 | 7,000-17,000 | 0.16-0.24 dL/g | Acid terminated | | 42-46° C. | <3 mo | 2% PVA | 128.9 | 0.048 | −13.4 ± 0.9 |

The present invention has been described in the following embodiments. Albeit, variations and some modifications described in the invention may be restored to without departing from the scope of the invention.

Example 12 (PLGA Biodegradable Nanoparticles)

In this example, single emulsion method was used to prepare polymer encapsulated carvedilol nanoparticles based on different types of PL(G)As (see table below). Briefly, Carvedilol is dissolved in Dichloromethane (DCM) as a 25 mg/mL stock solution. PLGA/PLA/PLA-PEG is prepared at the same concentration in DCM. Polymer to API at 10:1 ratio is optimized to prepare the oil (organic) phase by thorough vortex. 2% Poly (vinyl alcohol), PVA (Mw Example 13 (Polymeric Micro/Nanoparticles)

Formulation of Composition

Formula provides the formulation containing polysorbate 80, polyethylene glycol 4000 (PEG4000), sodium phosphate dibasic and sodium phosphate monobasic.

| Name | Concentration (mg/mL) |
|---|---|
| Carvedilol | 50 |
| Polysorbate 80 | 5 |
| PEG4000 | 10 |
| sodium phosphate dibasic | 6.0 |
| sodium phosphate monobasic | 7.1 |

Formulation Preparation

Polysorbate 80 was dissolved into water for injections by mixing. The solution was sterilized by filtration through a sterile 0.2 μm filter into a sterilized stainless steel container. Sterile grade carvedilol was dispersed into the solution and mixed until homogeneous. The suspension was milled aseptically in Planetary Mill PULVERISETTE 5 using 0.5 mm sterilized glass beads as grinding media until the required particle size was reached. The suspension was filtered aseptically through a 100 μm filter into a sterilized stainless steel container.

All the other excipients including PEG4000, sodium phosphate dibasic and sodium phosphate monobasic were added into water for injections and mixed well until dissolved. The solution was then sterilized by passing through a sterile 0.2 μm filter and transferred aseptically into the previous suspension. The suspension was mixed well until homogeneous and filled aseptically into sterile syringes.

| Particle size (nm) | PDI | Zeta-potential (mV) | DL (mg/ml) |
|---|---|---|---|
| 362 | 0.31 | −5.9 | 47.4 |

The formulation described herein can also be pre-milled with other surfactants such as polysorbate 20, polysorbate 40, polysorbate 60, polyoxyl 35 castor oil (Cremophor EL), polyoxyl 40 hydrogenated castor oil (Cremophor RH 40), polyoxyl 60 hydrogenated caster oid (Cremophor RH 60), Sorbitan monooleate (Span 20), d-α-Tocopheryl polyethylene glycol 1000 succinate (TPGS). To prepare the injectable solution, there are some other preferred excipients could be used, including PEG 300 caprylic/capric glycerides (Softigen 767), PEG 400 caprylic/capric glycerides (Labrasol), PEG 300 oleic glycerdies (Labrafil M-1944CS), polyoxyl 8 stearate (PEG 400 monosterate), polyxyl 40 stearate (PEG 1750 monosterate), PEG 3350, PEG 8000, poloxamer 124, poloxamer 237, poloxamer 338 and poloxamer 407.

Example 14 (Polymeric Micro/Nanoparticles)

Using the procedure from Example 13, the following microparticles was obtained and the particle size distribution was shown in FIG. 5.

| Particle Size Distribution | | | | | |
|---|---|---|---|---|---|
| D10 (um) | D50 (um) | D90 (um) | Mean (um) | Zeta-potential (mV) | DL (mg/mL) |
| 2.56 | 4.80 | 8.34 | 5.19 | −9.8 | 52.5 |

Example 15 (Polymeric Micro/Nanoparticles)

Formulation of Composition

The formula below provides the formulation containing polysorbate 80, poloxamer 188, mannitol, sodium phosphate dibasic and sodium phosphate monobasic.

| Name | Concentration (mg/mL) |
|---|---|
| Carvedilol | 50 |
| Poloxamer 188 | 10 |
| Polysorbate 80 | 5 |
| Mannitol | 5 |
| sodium phosphate dibasic | 6.0 |
| sodium phosphate monobasic | 7.1 |

Formulation Preparation

Polysorbate 80 was dissolved into water for injections by mixing and poloxamer 188 was added and mixed until homogeneous. The solution was sterilized by filtration through a sterile 0.2 μm filter into a sterilized stainless steel container. Sterile grade carvedilol was dispersed into the solution and mixed. The suspension was milled aseptically using LV1 Microfluidizer High Shear Fluid Processor until the required particle size was reached.

All the other excipients including mannitol, sodium phosphate dibasic and sodium phosphate monobasic were added into water for injections and mixed well until dissolved. The solution was then sterilized by passing through a sterile 0.2 μm filter and transferred aseptically into the previous suspension. The suspension was mixed well until homogeneous and filled aseptically into sterile syringes.

| Particle size (nm) | PDI | Zeta-potential (mV) | DL (mg/ml) |
|---|---|---|---|
| 276 | 0.16 | −12.7 | 48.2 |

What is claimed:

1. A parenteral drug delivery composition for sustained release, comprising:
   carvedilol encapsulated inside microparticles or nanoparticles forming liposomes,
   wherein the liposomes contain approximately 0.047% of the carvedilol,
   wherein the liposomes are in a size range of 0.05 microns to 0.3 microns in diameter,
   wherein the liposomes provide a longer residence time of the carvedilol in vivo, as compared to a free-carvedilol solution administered parenterally, and
   wherein the liposomes exhibit an in vitro release of greater than 80% of total drug for a minimum of 2 hours and an in vitro release of 80% of total drug for a minimum of 6 hours.

2. The composition of claim 1, wherein the microparticles or nanoparticles are biodegradable.

3. The composition of claim 2, wherein (i) the biodegradable formulation contains 0.001 to 30.0 percent (m/m) of the carvedilol or a pharmacologically acceptable salt thereof, (ii) the microparticles or the nanoparticles are in the size range of 0.02 to 20 microns in diameter, and (iii) the biodegradable formulation provides a longer residence time of the carvedilol in vivo, as compared to a free-carvedilol solution administered parenterally.

4. The composition of claim 3, wherein the biodegradable formulation includes about 0.001% to 30% m/m of the carvedilol or the pharmacologically acceptable salt thereof, and the drug loading in the microparticles or the nanoparticles is in the range of 0.1% to 90%, preferably 1% to 50%, and more preferably 10% to 30% (m/m).

5. The composition of claim 3, wherein a Z-average of a mean diameter of the microparticles or the nanoparticles is less than 20 micron, preferably less than 1000 nm, more preferably less than 500 nm, still more preferably less than 300 nm, even more preferably less than 200 nm, or much more preferably less than 100 nm.

6. The composition of claim 3, wherein the microparticles or the nanoparticles exhibits an in vitro release of 80% of total drug for a minimum of 2 hours, preferably an in vitro release of 80% of total drug for a minimum of 6 hours.

7. The composition of claim 1, wherein the microparticles or nanoparticles are polymeric.

8. The composition of claim 1, wherein the liposomes before dosing include between about 0.01 to 90 mole percent phospholipid(s), 0.01 to 70 mole percent cholesterol, and between about 0.01 to 90 mole percent of a negatively charged phospholipid.

9. The composition of claim 1, wherein a Z-average of a liposome mean diameter is less than 500 nm, preferably less than 300 nm, more preferably less than 200 nm, or even more preferably less than 100 nm.

10. A method of use of a pharmaceutical composition in a parenteral drug delivery system for sustained release of carvedilol, the method comprising:
   administering the pharmaceutical composition of claim 1 for treating mild to severe congestive heart failure (CHF), left ventricular dysfunction (LVD) following heart attack in human or animals who are otherwise stable, and for treating high blood pressure for human or animals under emergence and intense care or who cannot swallow an oral dosage form.

* * * * *